United States Patent
Chambaud et al.

(10) Patent No.: US 8,697,054 B2
(45) Date of Patent: Apr. 15, 2014

(54) **STRAIN OF *LACTOBACILLUS RHAMNOSUS***

(75) Inventors: Isabelle Chambaud, Issy les Moulineaux (FR); Artem Khlebnikov, Boulogne (FR); Anne-Catherine Villain, Juvisy sur Orge (FR); Gianfranco Grompone, Paris (FR); Thierry Saint Denis, Vincennes (FR)

(73) Assignee: Campagnie Gervais Danone, Paris (FR)

( * ) Notice: Subject to any disclaimer, the term of this patent is extended or adjusted under 35 U.S.C. 154(b) by 392 days.

(21) Appl. No.: 12/933,373

(22) PCT Filed: Mar. 18, 2009

(86) PCT No.: PCT/FR2009/000284
§ 371 (c)(1),
(2), (4) Date: Nov. 17, 2010

(87) PCT Pub. No.: WO2009/122042
PCT Pub. Date: Oct. 8, 2009

(65) Prior Publication Data
US 2011/0059058 A1     Mar. 10, 2011

(30) Foreign Application Priority Data
Mar. 19, 2008   (FR) .................................. 08 01507

(51) Int. Cl.
*A01N 63/00*   (2006.01)

(52) U.S. Cl.
USPC ..................... 424/93.45; 435/252.3; 536/23.7

(58) Field of Classification Search
None
See application file for complete search history.

(56) References Cited

U.S. PATENT DOCUMENTS 5,908,646 A * 6/1999 Mayra-Makinen et al. .... 426/36

FOREIGN PATENT DOCUMENTS

WO       WO 99/10476          3/1999

OTHER PUBLICATIONS

Ahmed, "Genetically modified probiotics in foods." (2003) Trends in Biotechnology, vol. 21: 491-497.*
Dunne et al. "In vitro selection criteria for probiotic bacteria of human origin: correlation with in vivo findings." (2001) American Journal of Clinical Nutrition, vol. 73 (supp.): 386S-392S.*
Gopal, et al., "In Vitro Adherence Properties of *Lactobacillus rhamnosus* DR20 . . . ", International Journal of Food Microbiology, 67, pp. 207-216, 2001.
Forestier, et al., "Probiotic Activities of *Lactobacillus casei rhamnosus*: In Vitro Adherence to Intestinal Cells . . . ", Res. Microbiol., 152, pp. 167-173, 2001.
Coudeyras, et al., "Taxonomic and Strain-Specific Identification of the Probiotic Strain . . . ", Applied and Enviornmental Microbiology, 74, pp. 2679-2689, 2008.
Adlerberth, et al., "A Mannose-Specific Adherence Mechanism in *Lactobacillus plantarum* Conferring . . . ", Applied and Enviornmental Microbiology, 62, 2244-2251, 1996.
Gill, et al., "Protection Against Translocating *Salmonoella typhimurium* Infection in Mice . . . ", Med. Microbiol. Immunol., 190, pp. 97-104, 2001.

* cited by examiner

*Primary Examiner* — Jon P Weber
*Assistant Examiner* — Teresa E Knight
(74) *Attorney, Agent, or Firm* — Morgan, Lewis & Bockius LLP

(57) ABSTRACT

The invention relates to a novel strain of *Lactobacillus rhamnosus*, having antimicrobial and immunomodulatory properties, and to compositions containing said strain.

5 Claims, 2 Drawing Sheets

STRAIN OF *LACTOBACILLUS RHAMNOSUS*

RELATED APPLICATIONS

The present application is a U.S. National Phase Application of International Application No. PCT/FR2009/000284 (filed Mar. 18, 2009) which claims priority to European Patent Application No. 0801507 (filed Mar. 19, 2008) which are hereby incorporated by reference in their entirety.

The invention relates to a novel strain of *Lactobacillus rhamnosus* having antimicrobial and immunomodulatory properties.

A large number of scientific studies have reported the beneficial effects, on the health, of certain microorganisms present in fermented foodstuffs, in particular dairy products. These microorganisms are commonly referred to as "probiotics". According to the definition generally accepted at the current time, probiotics are: "live microorganisms which, when they are consumed in appropriate amounts, have a beneficial effect on the health of the host" (FAO/WHO report on evaluation of health and nutritional properties of probiotics in food, including powder milk containing live lactic acid bacteria; Cordoba, Argentina; 1-4 Oct. 2001).

It has been shown that the consumption of food products containing probiotic bacteria can produce favorable effects on the health, in particular through re-equilibrating the intestinal flora, improving resistance to infections, and modulating the immune response.

The probiotic microorganisms used in human food are generally lactic acid bacteria belonging mainly to the *Lactobacillus* and *Bifidobacterium* genera.

However, the beneficial effects on the health are not generally common to all the bacteria of the same genus, nor even of the same species. They are, most commonly, encountered only in certain strains; in addition, the effects observed can vary qualitatively and/or quantitatively from one probiotic strain to the other, including within the same species.

In order for it to be possible for a microorganism to be considered potentially useful as a probiotic, it must meet at least one, and ideally several, of the following criteria:

- exhibit an inhibitory activity with respect to pathogenic microorganisms that may be present in the intestinal flora, it being possible for this activity to result either from the ability to adhere to the intestinal cells, thus excluding or reducing the adherence of the pathogens, or from the ability to produce substances which inhibit the pathogens, or from the combination of these two characteristics;
- exhibit immunomodulatory properties, and in particular immunostimulatory and/or anti-inflammatory properties.

In addition, if this microorganism is intended to be incorporated into a dairy product, it should preferably exhibit satisfactory growth on milk.

Finally, it should maintain good viability, during the production and storage of the foodstuff into which it is incorporated, and also after ingestion of this foodstuff by the consumer, so as to be able to reach the intestine and survive in the intestinal environment.

It should, however, be noted that, although viability is essential in order to correspond to the current definition of "probiotic", it has been shown that some of the beneficial effects associated with probiotic strains can be obtained even in the absence of live bacteria, and are attributable to certain bacterial fractions or to active fractions of their culture supernatants. For example, PCT application WO2004093898 describes an immunomodulatory preparation obtained by fractionation of the culture supernatant of the CNCM I-2219 strain.

The inventors have now succeeded in isolating a strain of *Lactobacillus rhamnosus* which meets the criteria indicated above.

A subject of the present invention is this strain, which was deposited according to the Treaty of Budapest, with the CNCM (Collection Nationale de Cultures de Microorganismes [National Collection of Microorganism Cultures], 25 rue du Docteur Roux, Paris), on Nov. 9, 2006, under number I-3690.

It has the following characteristics:

Morphology: small squat, sometimes coccoid, bacilli, isolated or in small chains.

Fermentation of the following sugars (results obtained on an api 50 CH strip-API MRS medium at 37° C. for 48 h): Ribose, galactose, D-glucose, D-fructose, D-mannose, L-sorbose, rhamnose, mannitol, sorbitol, Methyl-D glucoside, N-acetyl-glucosamine, arbutin, esculin, salicin, maltose, lactose, trehalose, melezitose, beta-gentiobiose, D-turanose, D-tagatose and gluconate.

It has, in addition, antimicrobial properties which result in a strong ability to inhibit the growth of pathogenic microorganisms in culture.

It also has properties of adhesion to mannose. It is known that mannose-rich glycoconjugates present at the surface of the intestinal epithelial cells play a role in the attachment of pathogenic bacteria, such as enterotoxic *Escherichia coli*, salmonellae, *Vibrio cholerae* or *Pseudomonas aeruginosa*, and it has been reported that the mannose-adhesion properties of certain probiotic bacteria enables them to compete with these pathogens, and to inhibit their adhesion to the intestinal mucosa, thus conferring anti-infective properties on them (Michail and Abernathy, Pediatr. Gastroenterol. Nutr., 35, 350-355 2002; Mangell et al., Dig Dis Sci., 47, 511-506, 2002). These properties had, however, been observed mainly on bacteria of the *Lactobacillus plantarum* species (in particular the *L. plantarum* strain 229v, described in application EP0817640 and the *L. plantarum* strain WCFS1), but not on bacteria of the *Lactobacillus rhamnosus* species.

The CNCM I-3690 strain also has immunomodulatory properties, and in particular anti-inflammatory properties.

The present invention also encompasses, as subject, *Lactobacillus rhamnosus* strains that can be obtained by mutagenesis or by genetic transformation of the CNCM I-3690 strain. Preferably, these strains retain at least the antimicrobial properties, or the immunomodulatory properties of the CNCM I-3690 strain. They may be strains in which one or more of the endogenous genes of the CNCM I-3690 strain has (have) been mutated, for example so as to modify some of its metabolic properties (e.g. the ability of this strain to metabolize sugars, its resistance to intestinal transit, its resistance to acidity, its post-acidification or its metabolite production). They may also be strains resulting from genetic transformation of the CNCM I-3690 strain with one or more gene(s) of interest, making it possible, for example, to confer additional physiological characteristics on said strain, or to express proteins of therapeutic or vaccine interest, which it is desired to administer by means of said strain.

These strains can be obtained from the CNCM I-3690 strain by means of the conventional techniques for random or site-directed mutagenesis and genetic transformation of lactobacilli, such as those described, for example, by Gury et al. (Arch Microbiol., 182, 337-45, 2004) or by Velez et al. (Appl Environ Microbiol., 73, 3595-3604, 2007), or by means of the technique known as "genome shuffling" (Patnaik et al. Nat Biotechnol, 20, 707-12, 2002; Wang Y. et al., J. Biotechnol., 129, 510-15, 2007).

A subject of the present invention is also cell fractions which can be obtained from a *Lactobacillus rhamnosus* strain in accordance with the invention. They are in particular DNA preparations or bacterial wall preparations obtained from cultures of said strain. They may also be culture supernatants or fractions of these supernatants.

A subject of the present invention is also compositions comprising a *Lactobacillus rhamnosus* strain in accordance with the invention, or a cell fraction obtained from said strain.

These compositions can in particular be lactic ferments, combining a *Lactobacillus rhamnosus* strain in accordance with the invention with one or more other, optionally probiotic, strain(s) of lactic acid bacteria.

They may also be food products, and in particular dairy products, or pharmaceutical or cosmetic products comprising a *Lactobacillus rhamnosus* strain in accordance with the invention, or a cell fraction obtained from said strain.

When said strain is present in the form of live bacteria, they will preferably be present in a proportion of at least $10^5$ cfu per gram, advantageously at least $10^6$ cfu per gram of product, more advantageously at least $10^7$ cfu per gram, and even more advantageously at least $10^8$ cfu per gram.

The present invention will be understood more clearly from the further description which follows, which refers to examples illustrating the antimicrobial immunomodulatory and anti-infective properties of the CNCM I-3690 strain.

EXAMPLE 1

Figure 1:
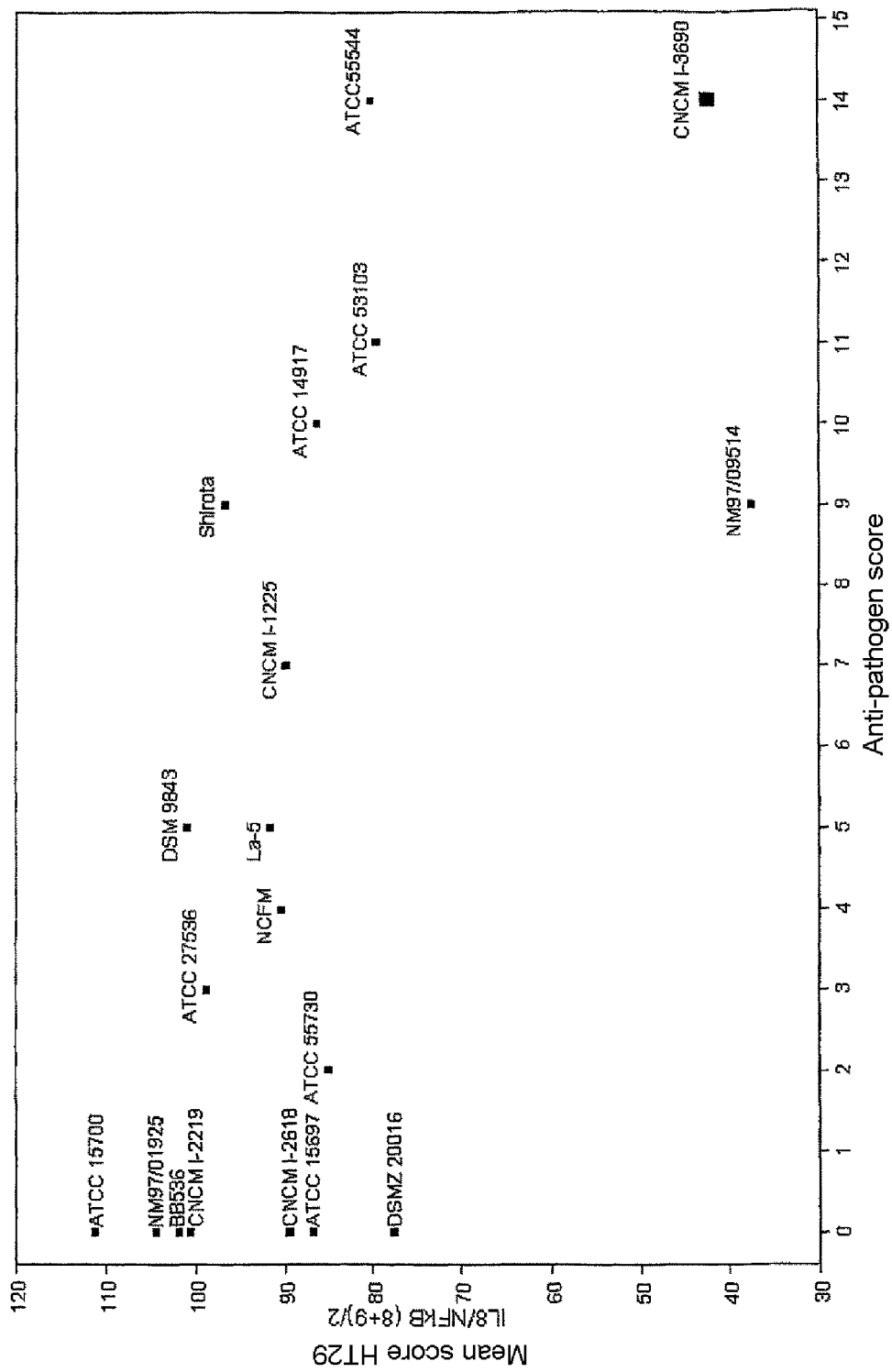
FIG. 1 illustrates that CNCM 1-3690 strain strongly inhibits the inflammatory response of the HT-29 epithelial cells and shows the point at which this strain stands out relative to the other strains tested.

Comparison of the Properties of the CNCM I-3690 Strain with Those of Known Probiotic Strains The properties of the CNCM I-3690 strain were compared with those of various strains of the prior art, known for their probiotic properties.

The list of these strains is given in table I below.

TABLE I

| Genus | Species | Name(s) | Publication number of patent applications |
|---|---|---|---|
| *Lactobacillus* | *johnsonii* | NCC533 = La1 = CNCM I-1225 | EP0577903 |
| *Lactobacillus* | *acidophilus* | NCFM | WO2004032639 |
| *Lactobacillus* | *acidophilus* | La-5 | |
| *Lactobacillus* | *casei* | Shirota | |
| *Lactobacillus* | *paracasei* | CRL431 = ATCC 55544 | |
| *Lactobacillus* | *rhamnosus* | LGG = ATCC 53103 | US4839281 |
| *Lactobacillus* | *rhamnosus* | HN001 = NM97/09514 | WO9910476 |
| *Lactobacillus* | *plantarum* | ATCC 14917 = DSMZ 20174 = WCFS1 | |
| *Lactobacillus* | *plantarum* | Probi 299v = DSM 9843 | WO9391823 |
| *Lactobacillus* | *reuteri* | DSMZ 20016 | |
| *Lactobacillus* | *reuteri* | Biogaia SD 2112: ATCC55730 | WO2004034808 |
| *Bifidobacterium* | *breve* | ATCC 15700 | |
| *Bifidobacterium* | *breve* | BBC50 = CNCM I-2219 | EP1189517 |
| *Bifidobacterium* | *infantis* | ATCC 15697 | |
| *Bifidobacterium* | *longum* | BB536 | |
| *Bifidobacterium* | *longum* | NCC2705 = CNCM I-2618 | |
| *Bifidobacterium* | *animalis* subsp. *lactis* | BB12 = ATCC 27536 | |
| *Bifidobacterium* | *animalis* subsp. *lactis* | HN019 = NM97/01925 | WO9910476 |

Materials and Methods

1—Antimicrobial Activity

The investigation of antimicrobial activities was carried out against three target pathogenic bacteria: *Escherichia coli* E1392-75-2A, *Salmonella enteritidis* NIZO B1241 and *Listeria monocytogenes* 4B. The lactic acid bacteria were cultured on Petri dishes in various media: LM17 (M17 medium (Terzaghi & Sandine, Appl. Microbiol. 29, 807-813, 1975) supplemented with 1% of lactose, Elliker medium (Elliker et al., J. Dairy Sci., 39, 1611-1612, 1956), and TGE medium (Tryptone-Glucose-Meat Extract).

The dishes are incubated at 37° C. until bacterial colonies appear. The *Bifidobacterium* cultures were carried out under anaerobic conditions. A layer of agar containing BHI (brain-heart infusion) medium and the pathogen is then poured at the surface of the dishes. The dishes are incubated again at 37° C., for 24 h. The diameters of the areas of pathogen inhibition are then measured around each colony of lactic acid bacteria. Score 1 corresponds to a diameter of between 1 and 3 mm. Score 2 corresponds to a diameter of between 4 and 6 mm. Score 3 corresponds to a diameter of greater than 6 mm. Each experiment was carried out three times independently for each strain.

The scores obtained on the target pathogens in each experiment were added, so as to obtain, for each lactic acid bacterium, an overall score for antimicrobial activity.

The results are given in table II hereinafter.

These results show that, among the strains tested, the CNCM I-3690 strain is, with the ATCC55544 strain, the one which has the highest antimicrobial activity.

TABLE II

| Genus | Species | Reference | (1) coli/ Elliker | (2) coli/ LM17 | (3) Listeria/ Elliker | (4) Listeria/ TGE | (5) Listeria/ LM17 | (6) Salmo- nella/ Elliker | (7) Salmo- nella/ TGE | Anti-pathogen score (1 + 2 + 3 + 4 + 5 + 6 + 7) |
|---|---|---|---|---|---|---|---|---|---|---|
| Lactobacillus | rhamnosus | DN 116 010 or CNCM I-3690 | 2 | 1 | 3 | 2 | 0 | 3 | 3 | 14 |
| Lactobacillus | paracasei | CRL431 = ATCC55544 | 2 | 0 | 3 | 3 | 1 | 3 | 2 | 14 |
| Lactobacillus | rhamnosus | LGG = ATCC 53103 | 2 | 0 | 1 | 2 | 0 | 3 | 3 | 11 |
| Lactobacillus | plantarum | ATCC 14917 = DSMZ 20174 = WCFS1 | 2 | 0 | 1 | 2 | 0 | 3 | 2 | 10 |
| Lactobacillus | casei | Shirota | 2 | 0 | 3 | 1 | 0 | 1 | 2 | 9 |
| Lactobacillus | rhamnosus | HN001 = NM97/09514 | 1 | 0 | 1 | 2 | 0 | 3 | 2 | 9 |
| Lactobacillus | johnsonii | NCC533 = La1 = I-1225 | 1 | 0 | 1 | 1 | 1 | 2 | 1 | 7 |
| Lactobacillus | plantarum | Probi 299v = DSM 9843 | 1 | 0 | 1 | 1 | 0 | 1 | 1 | 5 |
| Lactobacillus | acidophilus | La-5 | 1 | 0 | 1 | 2 | 0 | 0 | 1 | 5 |
| Lactobacillus | acidophilus | NCFM | 1 | 0 | 1 | 1 | 0 | 0 | 1 | 4 |
| Bifidobacterium | animalis subsp. lactis | BB12 = ATCC 27536 | 1 | 0 | 0 | 0 | 0 | 0 | 2 | 3 |
| Lactobacillus | reuteri | Biogaia SD 2112 ATCC55730 | 0 | 0 | 1 | 0 | 0 | 1 | 0 | 2 |
| Bifidobacterium | longum | BB536 | 0 | 0 | 0 | 0 | 0 | 0 | 0 | 0 |
| Bifidobacterium | animalis subsp. lactis | HN019 = NM97/01925 | 0 | 0 | 0 | 0 | 0 | 0 | 0 | 0 |
| Lactobacillus | reuteri | DSMZ 20016 | 0 | 0 | 0 | 0 | 0 | 0 | 0 | 0 |
| Bifidobacterium | infantis | ATCC 15697 | 0 | 0 | 0 | 0 | 0 | 0 | 0 | 0 |
| Bifidobacterium | breve | BBC50 = I-2219 | 0 | 0 | 0 | 0 | 0 | 0 | 0 | 0 |
| Bifidobacterium | breve | ATCC 15700 | 0 | 0 | 0 | 0 | 0 | 0 | 0 | 0 |
| Bifidobacterium | longum | NCC2705 = CNCM I-2618 | 0 | 0 | 0 | 0 | 0 | 0 | 0 | 0 |

2—Immunomodulation

The immunomodulatory properties of the various lactic acid bacteria were evaluated by detection of the modulation induced, by these bacteria, on the inflammatory response of colon epithelial cells (HT-29), by measuring the effect of these bacteria on the activation of the transcriptional regulator NF-κB and the secretion of the pro-inflammatory cytokine IL-8 by the HT-29 cells in the presence of a mixture of TNFα, IL-1β and IFNγ (Cytomix) simulating the conditions of an inflammatory attack.

Culturing of Lactic Acid Bacteria

The growth of the lactic acid bacteria takes place in MRS medium (De Man et al., J. Appl. Bacteriol. 23, 130-135, 1960), or MRS medium supplemented with L-cysteine (1% final concentration), or in Elliker medium, depending on the bacterial species tested. The bacteria were inoculated and cultured in a first preculture of 10 mL, for 16 h at 37° C., and recultured the following day in a second culture in 100 mL, for 16 h at 37° C., and harvested at the end of the stationary phase.

Culturing and Preparation of Cells

The HT29 cells are maintained at 37° C. and 5% $CO_2$ in Dulbecco's Modified Eagle Medium (DMEM) supplemented with 4.5 g/L of D-Glucose, L-Glutamine (1 mM final concentration), nonessential amino acids (AA) (1% final concentration), penicillin/streptomycin (1% final concentration) and fetal calf serum (FCS) (10% final concentration).

The HT-29 cells are seeded into 12-well plates in a proportion of $2 \times 10^5$ cells per well in 2 ml of medium, two days before the experiments regarding interaction with the bacteria and stimulation with the Cytomix.

For measuring the activation of the transcriptional regulator NF-κB, the cells are transfected, on the day after the seeding, with the Ig-κB-Luciferase reporter plasmid, as described by Tien et al. (J. Immunol., 176, 1228-37, 2006).

Prior to the transfection, the cells are washed and the medium is replaced with the same medium without antibiotics. The transfection is performed by depositing, in each well, 100 μL of a mixture containing 75 ng of pIg-κB-luciferase plasmid and 1 μL of Lipofectamine 2000 in 99 μL of OptiPro medium. The plates are then incubated for 24H at 37° C. and 5% $CO_2$.

Interaction with the Bacteria and Stimulation with the Cytomix

The bacteria are recovered at the end of the stationary phase, and washed twice with PBS, before being interacted with the cells.

They are then incubated for 2 hours with the bacteria, with a multiplicity of infection of 100 bacteria per cell. After two hours of interaction with the bacteria, the cells are incubated for 6 hours in the presence of the bacteria and of the Cytomix, in a proportion of 50 ng/mL of TNFα, 2.5 ng/mL of IL-1β and 7.5 ng/mL of IFNγ in the incubation medium. All the incubations are carried out at 37° C. and 5% $CO_2$.

In order to determine the basal level of NF-κB activation and IL-8 secretion in the absence of lactic acid bacteria, the same experiment was carried out with the Cytomix stimulation being performed for 6 hours, after two hours of incubation of the cells in the absence of bacteria.

At the end of the 8 hours of incubation, 1 mL of medium is recovered in order to assay the secreted IL8. This assay is carried out by ELISA using the "QuantiGlo Human IL-8 chemiluminescent ELISA" kit (R&D Systems).

For measuring the NF-κB activation, the cells are lysed in 100 microliters of a buffer (25 mM Tris, pH 7.9, 8 mM $MgCl_2$, 1% Triton, 15% Glycerol), supplemented with 1 mM DTT. For measuring the luciferase activity, 10 microliters of cell lysate are added to reading buffer (25 mM Tris, pH 7.9, 8 mM $MgCl_2$, 1% Triton, 15% Glycerol), supplemented with 1 mM DTT, 100 mM ATP and 2 mM of Luciferin/$K_2HPO_4$-pH 7.58. The measurement is carried out using a luminometer (Beckman Coulter).

After this total interaction time of 8 hours, the NF-κB activation and the IL-8 secretion are measured.

The NF-κB activation and IL-8 secretion values are expressed as percentages relative to the basal layer observed in the absence of lactic acid bacteria. For each strain tested, an average immunomodulation score is calculated by adding the percentage NF-κB activation and the percentage IL-8 secretion. These results are given in table III below.

TABLE III

| Genus | Species | Reference | NFκB-HT29 (8) | IL8-HT29 (9) | Mean score HT29 IL8/NFκB (8 + 9)/2 |
|---|---|---|---|---|---|
| Lactobacillus | rhamnosus | DN 116 010 or CNCM I-3690 | 34.7 | 49.7 | 42 |
| Lactobacillus | paracasei | CRL431 = ATCC55544 | 58.7 | 101.5 | 80 |
| Lactobacillus | rhamnosus | LGG = ATCC 53103 | 78.0 | 81.0 | 80 |
| Lactobacillus | plantarum | ATCC 14917 = DSMZ 20174 = WCFS1 | 80.7 | 91.9 | 86 |
| Lactobacillus | casei | Shirota | 94.0 | 99.7 | 97 |
| Lactobacillus | rhamnosus | HN001 = NM97/09514 | 25.0 | 49.7 | 37 |
| Lactobacillus | johnsonii | NCC533 = La1 = I-1225 | 86.9 | 92.7 | 90 |
| Lactobacillus | plantarum | Probi 299v = DSM 9843 | 93.9 | 107.7 | 101 |
| Lactobacillus | acidophilus | La-5 | 93.8 | 89.5 | 92 |
| Lactobacillus | acidophilus | NCFM | 85.8 | 95.0 | 90 |
| Bifidobacterium | animalis subsp. lactis | BB12 = ATCC 27536 | 99.4 | 98.0 | 99 |
| Lactobacillus | reuteri | Biogaia SD 2112 ATCC55730 | 82.0 | 87.9 | 85 |
| Bifidobacterium | longum | BB536 | 111.6 | 92.0 | 102 |
| Bifidobacterium | animalis subsp. lactis | HN019 = NM97/01925 | 107.7 | 101.2 | 104 |
| Lactobacillus | reuteri | DSMZ 20016 | 71.4 | 83.6 | 78 |
| Bifidobacterium | infantis | ATCC 15697 | 77.5 | 96.3 | 87 |
| Bifidobacterium | breve | BBC50 = I-2219 | 97.5 | 103.6 | 101 |
| Bifidobacterium | breve | ATCC 15700 | 117.7 | 104.6 | 111 |
| Bifidobacterium | longum | NCC2705 = CNCM I-2618 | 87.8 | 91.4 | 90 |

These results show that the CNCM I-3690 strain strongly inhibits the inflammatory response of the HT-29 epithelial cells. Among the other strains tested, only the HN001 strain has comparable anti-inflammatory properties.

3—Survival with Respect to Gastric and Intestinal Stresses

An in vitro model reflecting the conditions of gastric stress and intestinal stress was used.

Cultures of lactic acid bacteria were prepared in milk supplemented with yeast extract. The cultures are incubated for 24 to 48 h, depending on the species (until the stationary phase of the culture).

Intestinal Stress:

An artificial intestinal juice composed of porcine bile salts (at 3.3 g/l) and of NaHCO$_3$ carbonate buffer (at 16.5 g/l) is prepared. The pH is adjusted to 6.3. 1 ml of this intestinal juice is added to 100 μl of bacterial culture. The cultures are then incubated for 5 hours. Next, the bacterial populations before and after the stress are evaluated on dishes.

Gastric Stress:

An artificial gastric juice is prepared. It is composed of lactic acid (9 g/l), pepsin (3.5 g/l) and NaCl (2.2 g/l). The pH is adjusted to 3.1. 1 ml of this artificial juice is added to 100 μl of bacterial culture. The cultures are incubated for various times: 10 min, 30 min and 60 min. The bacterial populations are evaluated on dishes.

The values are expressed in the following way:

Gastric stress=mean [log(cfu 10 min/cfu 0) and log(cfu 0/cfu 0)]×10+mean [log(cfu 30 min/cfu 0) and log (cfu 10 min/cfu 0)]×20+mean [log(cfu 60 min/cfu 0) and log (cfu 30 min/cfu 0)]×30.

Intestinal stress=log(cfu 5 h/cfu 0 h).

cfuXmin being the concentration of bacteria expressed as colony forming units (CFU) after X minutes of incubation.

For the gastric stress, survival is good when the value is greater than −50, moderately good when the value is between −50 and −100 and poor when the value is less than −100.

For the intestinal stress, survival is good when the value is greater than −0.5, moderately good when the value is between −0.5 and −1.5 and poor when the value is less than −1.5.

The results are given in the following table IV.

TABLE IV

| Genus | Species | Reference | Intestinal stress | Gastric stress |
|---|---|---|---|---|
| Lactobacillus | rhamnosus | DN 116 010 or CNCM I-3690 | 0.31 | −31.9 |
| Lactobacillus | paracasei | CRL431 = ATCC55544 | 0.04 | −47.4 |
| Lactobacillus | rhamnosus | LGG = ATCC 53103 | −0.07 | −44.0 |
| Lactobacillus | plantarum | ATCC 14917 = DSMZ 20174 = WCFS1 | −0.79 | −68.5 |
| Lactobacillus | casei | Shirota | −1.50 | −139.2 |
| Lactobacillus | rhamnosus | HN001 = NM97/09514 | 0.00 | −86.3 |

TABLE IV-continued

| Genus | Species | Reference | Intestinal stress | Gastric stress |
|---|---|---|---|---|
| Lactobacillus | johnsonii | NCC533 = La1 = I-1225 | 0.69 | 20.3 |
| Lactobacillus | plantarum | Probi 299v = DSM 9843 | −1.04 | −29.7 |
| Lactobacillus | acidophilus | La-5 | −0.23 | 43.3 |
| Lactobacillus | acidophilus | NCFM | −1.45 | −63.0 |
| Bifidobacterium | animalis subsp. lactis | BB12 = ATCC 27536 | 0.07 | −70.0 |
| Lactobacillus | reuteri | Biogaia SD 2112 ATCC55730 | 1.00 | −4.6 |
| Bifidobacterium | longum | BB536 | −1.12 | −438.7 |
| Bifidobacterium | animalis subsp. lactis | HN019 = NM97/01925 | 3.40 | 114.0 |
| Lactobacillus | reuteri | DSMZ 20016 | −1.91 | −80.0 |
| Bifidobacterium | infantis | ATCC 15697 | 2.79 | −412.9 |
| Bifidobacterium | breve | BBC50 = I-2219 | −0.91 | −333.8 |
| Bifidobacterium | breve | ATCC 15700 | −0.14 | −370.2 |
| Bifidobacterium | longum | NCC2705 = CNCM I-2618 | −0.22 | −319.2 |

The results illustrated in tables II, III and IV above show that, among the various strains tested, the CNCM I-3690 strain is the only one to have both considerable antimicrobial properties and considerable anti-inflammatory properties, accompanied, in addition, by very good properties of resistance to gastric and intestinal stresses.
To illustrate the superiority of this strain, the various scores obtained by this strain from the antimicrobial point of view were added together and a mean was calculated between the results obtained by this strain from the immunomodulation point of view. FIG. 1 shows the point at which this strain stands out relative to the other strains tested.

EXAMPLE 2

Mannose-Adhesion Properties of the CNCM I-3690 Strain

The ability of the CNCM I-3690 strain to adhere specifically to mannose was determined by means of an agglutination test. This test is based on the presence of mannose-containing polysaccharides at the surface of *Saccharomyces cerevisiae* cells. When bacteria adhering to mannose are brought into contact with *S. cerevisiae*, an agglutination phenomenon, which is visible under a microscope, occurs.

This model makes it possible to evaluate potential anti-infective properties of a bacterium, resulting from its ability to compete with pathogens at the level of adhesion to the intestinal mucosa.
The *L. plantarum* 229v and *L. plantarum* WCFS1 strains, known for their strong mannose-adhesion capacity, were used as positive controls.
The *Lactobacillus* strains are cultured in MRS medium, at a temperature of 37° C. The growth of the bacteria is arrested in the stationary phase, and the bacteria are then washed and their concentration is adjusted. The culturing of *S. cerevisiae* is carried out in "malt extract" medium (Oxoid).
A volume of 5 µl of bacterial suspension is then mixed with PBS or methyl-α-D-mannopyranoside (final concentration: 25 mM). 100 µl of a preparation containing 1% of *S. cerevisiae* cells are then added. The mixture is stirred for 10 min at ambient temperature, and then examined under a microscope, and the scores are attributed using the following grading:
Score 0=no agglutination
Score 1=weak agglutination
Score 3=strong agglutination
Score 5=very strong agglutination.
The experiment is carried out three times independently for each strain.
The results are given in table V hereinafter.

TABLE V

| Genus | Species | Reference | Mannose score |
|---|---|---|---|
| Lactobacillus | rhamnosus | DN 116 010 or CNCM I-3690 | 3 |
| Lactobacillus | paracasei | CRL431 = ATCC55544 | 0 |
| Lactobacillus | rhamnosus | LGG = ATCC 53103 | 0 |
| Lactobacillus | plantarum | ATCC 14917 = DSMZ 20174 = WCFS1 | 3 |
| Lactobacillus | casei | Shirota | 0 |
| Lactobacillus | rhamnosus | HN001 = NM97/09514 | 0 |
| Lactobacillus | johnsonii | NCC533 = La1 = I-1225 | 0 |
| Lactobacillus | plantarum | Probi 299v = DSM 9843 | 3 |
| Lactobacillus | acidophilus | La-5 | 0 |
| Lactobacillus | acidophilus | NCFM | 0 |
| Bifidobacterium | animalis subsp. lactis | BB12 = ATCC 27536 | 0 |
| Lactobacillus | reuteri | Biogaia SD 2112 ATCC55730 | 0 |
| Bifidobacterium | longum | BB536 | 0 |
| Bifidobacterium | animalis subsp. lactis | HN019 = NM97/01925 | 0 |
| Lactobacillus | reuteri | DSMZ 20016 | 0 |
| Bifidobacterium | infantis | ATCC 15697 | 0 |
| Bifidobacterium | breve | BBC50 = I-2219 | 0 |

TABLE V-continued

| Genus | Species | Reference | Mannose score |
|---|---|---|---|
| *Bifidobacterium* | *breve* | ATCC 15700 | 0 |
| *Bifidobacterium* | *longum* | NCC2705 = CNCM I-2618 | 0 |

It is observed that the percentage of *S. cerevisiae* cells agglutinated by the CNCM I-3690 strain is comparable to the percentage of *S. cerevisiae* cells agglutinated by the *L. plantarum* 229β and *L. plantarum* WCFS1 strains.

EXAMPLE 3

Growth of the CNCM I-3690 Strain on Milk

The growth-on-milk properties of the CNCM I-3690 strain were tested using the following protocol:

A medium constituted of skimmed milk reconstituted with water to which skimmed milk powder has been added was inoculated with the CNCM I-3690 strain, at levels ranging between $5.5 \times 10^6$ cfu/g and $3.3 \times 10^7$ cfu/g.

The fermentative activity of the strain, which is linked to its growth, is measured by continuously monitoring the pH of the growth medium.

Figure 2:
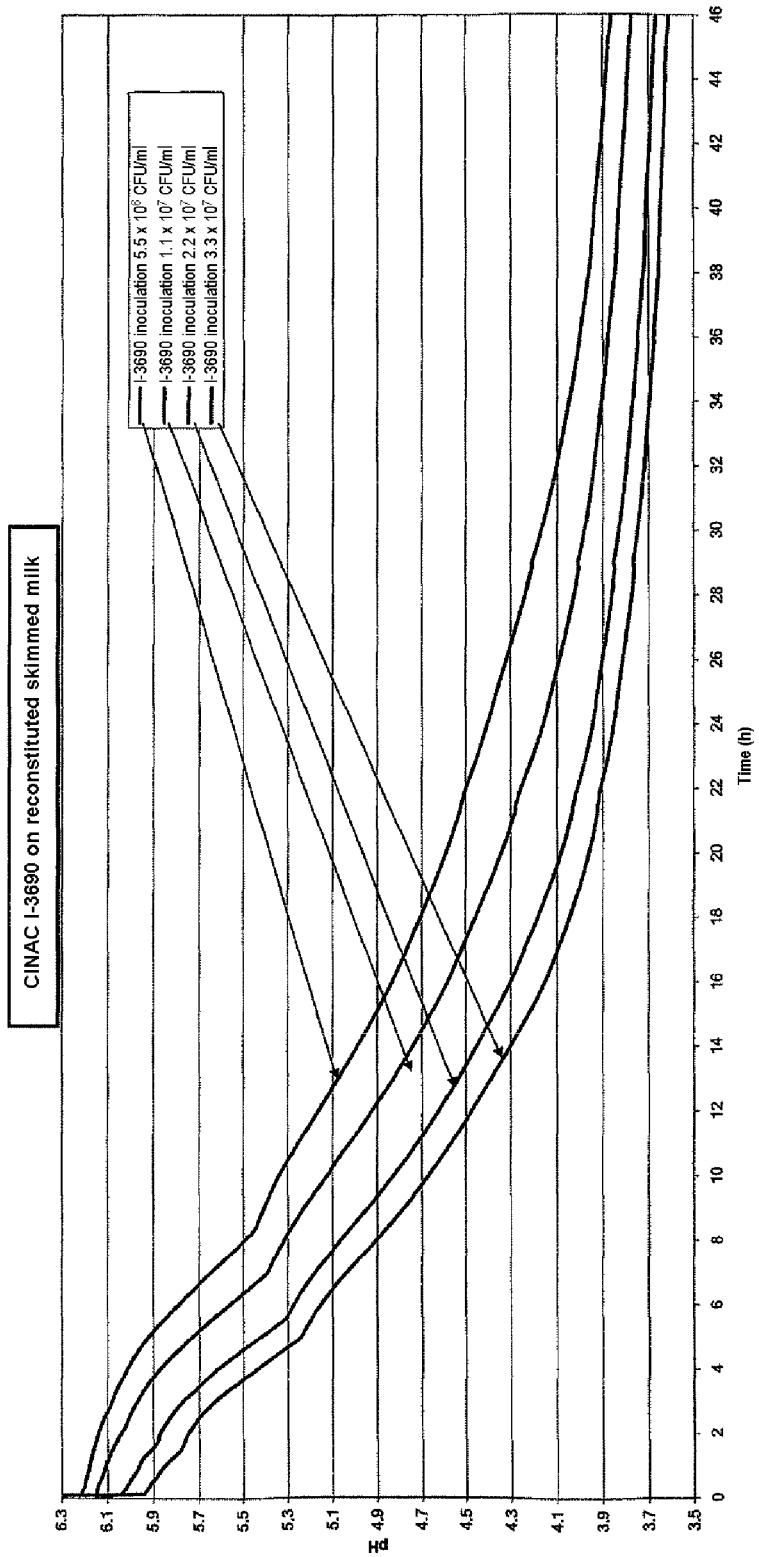
FIG. 2 illustrates that CNCM 1-3690 strain is capable of growing efficiently on milk.

The results are illustrated by FIG. 2.

These results show that the CNCM I-3690 strain is capable of growing efficiently on milk, and that it can therefore be used in the manufacture of fermented dairy products.

The invention claimed is:

1. An isolated *Lactobacillus rhamnosus* strain having antimicrobial, immunomodulatory and mannose-specific adhesion properties, wherein the *Lactobacillus rhamnosus* strain is deposited with the Collection Nationale de Cultures de Microorganismes (CNCM) under Accession number I-3690, or a mutant of the *Lactobacillus rhamnosus* I-3690 strain having all the identifying characteristics of I-3690.

2. A composition comprising the isolated *Lactobacillus rhamnosus* strain as claimed in claim 1.

3. The composition as claimed in claim 2, wherein the composition is a food product.

4. A method of treating a microbial infection in a subject comprising administering the *Lactobacillus rhamnosus* strain as claimed in claim 1.

5. A method of reducing inflammation in a subject comprising administering the *Lactobacillus rhamnosus* strain as claimed in claim 1.

* * * * *